United States Patent [19]

Mohrbacher et al.

[11] 4,031,079

[45] June 21, 1977

[54] INTERMEDIATES FOR 2-AMINOBENZODIAZEPINE-5-ONES

[75] Inventors: Richard J. Mohrbacher, Maple Glen; Philip P. Grous, Philadelphia, both of Pa.

[73] Assignee: McNeil Laboratories, Incorporated, Fort Washington, Pa.

[22] Filed: June 23, 1976

[21] Appl. No.: 699,097

Related U.S. Application Data

[62] Division of Ser. No. 615,667, Sept. 22, 1975.

[52] U.S. Cl. .................. 260/239.3 D; 260/465 D; 260/518 R; 424/244; 424/274

[51] Int. Cl.² ............. C07D 243/20; C07D 243/22

[58] Field of Search ............................ 260/239.3 D

[56] References Cited

UNITED STATES PATENTS

| | | | |
|---|---|---|---|
| 3,173,912 | 3/1965 | Krapcho | 260/239.3 D |
| 3,678,038 | 7/1972 | Field et al. | 260/239.3 D |

*Primary Examiner*—Henry R. Jiles
*Assistant Examiner*—Robert T. Bond
*Attorney, Agent, or Firm*—Salvatore R. Conte

[57] ABSTRACT

Compounds of the class of 2-amino-3,4-dihydro-4-loweralkyl-5H-1,4-benzodiazepine-5-ones useful as CNS depressants and hypotensive agents.

2 Claims, No Drawings

INTERMEDIATES FOR 2-AMINOBENZODIAZEPINE-5-ONES

DESCRIPTION OF THE INVENTION

This is a division of our copending Application Ser. No. 615,667, filed Sept. 22, 1975.

The novel 2-aminobenzodiazepine-5-ones of this invention may be structurally represented by the formula:

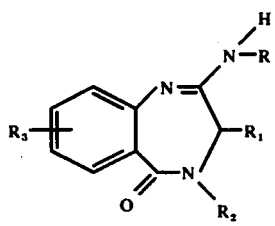

wherein:
R is a member selected from the group consisting of hydrogen, arylloweralkyl, indolylloweralkyl, diloweralkylaminoloweralkyl, and aryl;
$R_1$ is a member selected from the group consisting of hydrogen and aryl, preferably phenyl;
$R_2$ is loweralkyl, preferably methyl; and
$R_3$ is a member selected from the group consisting of hydrogen, halo, nitro, loweralkoxy, and loweralkyl; preferably hydrogen and halo;
provided that;
when said R is hydrogen, then said $R_1$ is aryl.

As used herein, "aryl" includes phenyl, trifluoromethyl-phenyl and substituted phenyl. "Substituted phenyl", as used herein, means phenyl with from one to three substituents each selected from the group consisting of halo, loweralkyl, hydroxy, and loweralkoxy. "Loweralkyl" and "loweralkoxy" may be straight or branched chained and have from one to five carbon atoms. The term "halo" is generic to chloro, bromo, iodo, and fluoro, preferably chloro.

The therapeutically active non-toxic acid addition salts of the subject compounds are also embraced within the scope of this invention.

The novel 2-aminobenzodiazepine-5-ones of formula (I) are readily obtained by the reaction of an appropriate benzodiazepine-2,5-dione of formula (II) with an unsubstituted amine or an appropriately substituted primary amine of formula (III), wherein R is as previously defined, in the presence of $TiCl_4$ in a suitable aprotic organic solvent. The amine (III) is in stoichiometric excess of the benzodiazepine-2,5-dione (II), preferably at a ratio of 5:1, respectively. The $TiCl_4$ is also preferably in stoichiometric excess. Suitable organic solvents include ethers, such as, for example, tetrahydrofuran (THF), dioxane, monoglyme and the like.

It should be noted that in the case of formation of the formula (I) compounds wherein R is:

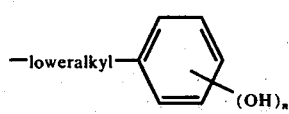

in which n is an integer from 1 to 3, the appropriate amine is a benzyloxyphenloweralkyl amine of the formula:

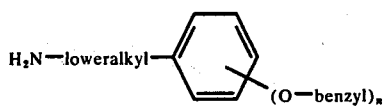

The resulting novel intermediates, 2-(benzyloxyphenloweralkylamino)-benzodiazepine-5-ones, of the formula:

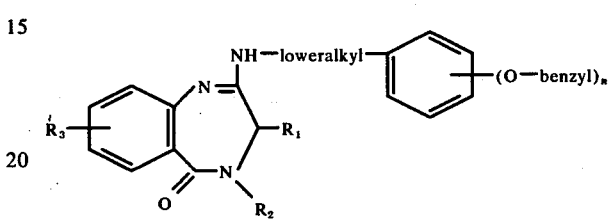

are then subjected to catalytic hydrogenation, for example, by treatment with $H_2$ in the presence of a metallic catalyst such as palladium, platinum, Raney nickel and the like, preferably under pressure, in order to debenzylate such intermediates and yield the desired hydroxyphenylloweralkyl derivatives of formula (I).

The reaction mixture may be heated, preferably under reflux, to enhance the rate of reaction.

An alternate method of synthesis of the subject compounds (I) involves reacting the formula (II) benzodiazepine-2,5-diones with $P_2S_5$ in a suitable organic solvent such as, for example, pyridine and the like, and ethers such as, for example, THF, dioxane, monoglyme and the like, to form as novel intermediates, the 2-thiobenzodiazepine-2,5-diones of formula (IV). From this point either of two routes may be taken to form the subject compounds (I).

Compounds of formula (IV) may be transformed into those of formula (I) directly by reaction with an appropriate amine of formula (III). The amine is used preferably in slight stoichiometric excess. The reactants are utilized either without solvent if the amine is a liquid or with a suitable organic solvent such as, for example, acetonitrile, pyridine and the like, and ethers such as, for example, THF, dioxane and the like. Elevated temperatures may be advantageously employed to enhance the rate of reaction.

An alternate route involves methylating the formula (IV) compounds to another set of novel intermediates, the 2-methylthiobenzodiazepine-5-ones of formula (IVa). Suitable methylating agents include, for example, $CH_3I$/NaH in an aromatic hydrocarbon solvent, for example, benzene, toluene, xylene and the like, dimethylsulfate (DMS)/aqueous NaOH, and the like. Another route of methylation employs methyl fluorosulfonate as the methylating agent in a chlorinated hydrocarbon solvent such as, for example, chloroform, methylene dichloride and the like. The methylated product (IVa) is then treated with an appropriate amine (III) as heretofore described to yield the desired final products (I).

The foregoing reactions may be schematically illustrated by the following diagram:

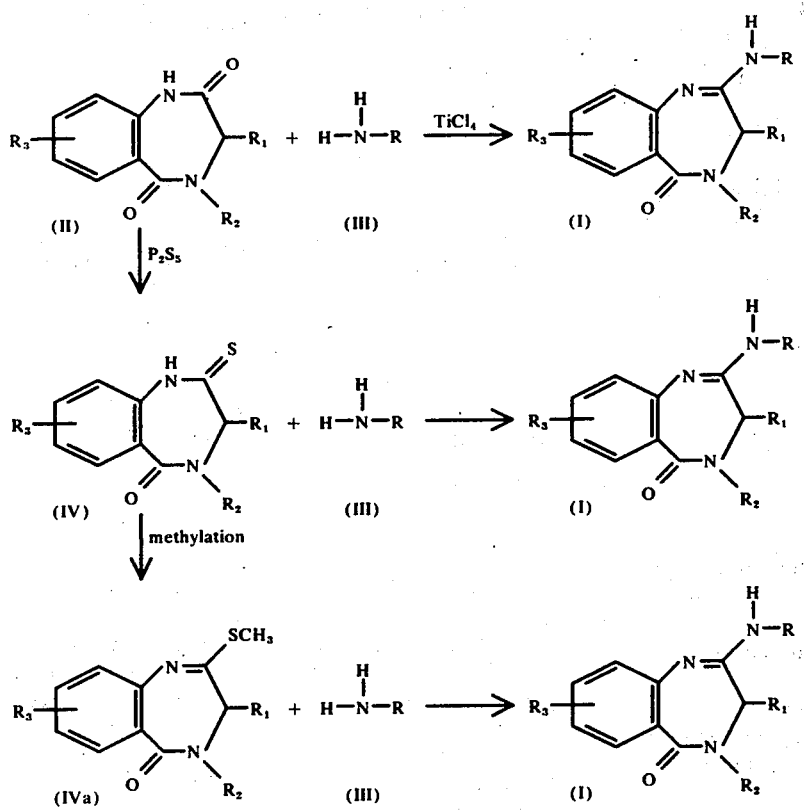

The diones of formula (II) wherein $R_1$ is hydrogen are described in the literature. However, those diones of formula (II) having an aryl group (Ar) as $R_1$ are novel. They may be prepared via a two step synthetic route. An appropriate o-nitrobenzoyl chloride of formula (V) is reacted with a cooled solution (0°–10° C) of, preferably, an equivalent amount of an appropriate α-aryl-N(loweralkyl)amino acid of formula (VI) in the presence of a suitable base, such as an alkali metal hydroxide, to neutralize the acid liberated during the course of the reaction. Should an acid addition salt form of (VI) be initially employed, an additional equivalent of base is preferably used to neutralize said salt to the corresponding free base form. The resultant solution of the alkali metal salt of (VII) is then treated with an appropriate acid such as, for example, a concentrated mineral acid, e.g. HCl, HBr and the like, to precipitate out the novel acid precursor, β-loweralkyl-o-nitro-α-arylhippuric acid of formula (VII). This acid precursor is then subjected to catalytic hydrogenation, e.g., by reaction with $H_2$ in 95% ethanol in the presence of a catalytic amount of platinum oxide in a Parr hydrogenerator, to give the diones of formula (II) wherein $R_1$ is aryl.

The reaction described above may be illustrated as follows:

Another method for the synthesis of the subject compounds (I), wherein R is hydrogen and $R_1$ is aryl, also begins with the formula (V) o-nitrobenzoyl chlorides. The addition of (V) to a cooled solution (0–10° C) of an equivalent amount of an appropriate N-loweralkyl-α-aryl-glycinitrile of formula (VIII) and a strong organic base such as, for example, triethylamine, N-methylpiperidine and the like, in an appropriate organic solvent, such as, for example, 1,2-dichloroethane, chloroform, dimethoxyethane and the like, produces the novel intermediate, β-loweralkyl-o-nitro-α-aryl-hippuronitrile of formula (IX). After the reactants have been mixed together, the temperature may be elevated to ambient temperature. This novel intermediate (IX) is also catalytically hydrogenated under conditions previously described to form another intermediate, the 3-aryl-1-hydroxy-2-imino-4-loweralkyl-1,2,3,4-tetrahydro-5H-1,4-benzodiazepine-5-one of formula (X). A solution of (X) in a suitable organic solvent such, as for example, a loweralkanol and the like, is then added to a solution of sodium dithionite ($Na_2S_2O_4$), the latter preferably being in a two-fold stoichiometric excess, to produce the subject compounds of formula (I) with R as hydrogen and $R_1$ as aryl. The reaction mixture may be heated, preferably under reflux conditions, to enhance the rate of reaction. The

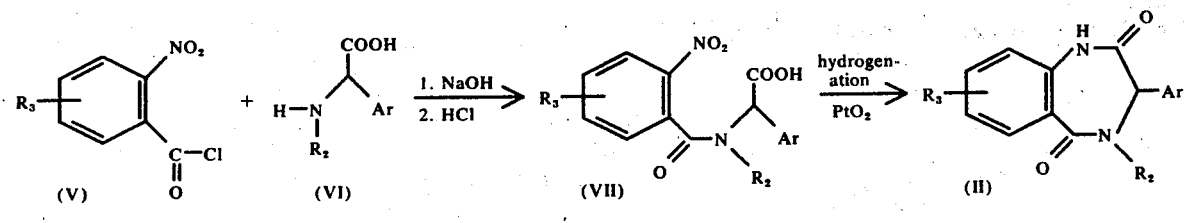

reaction scheme described above may be illustrated as follows:

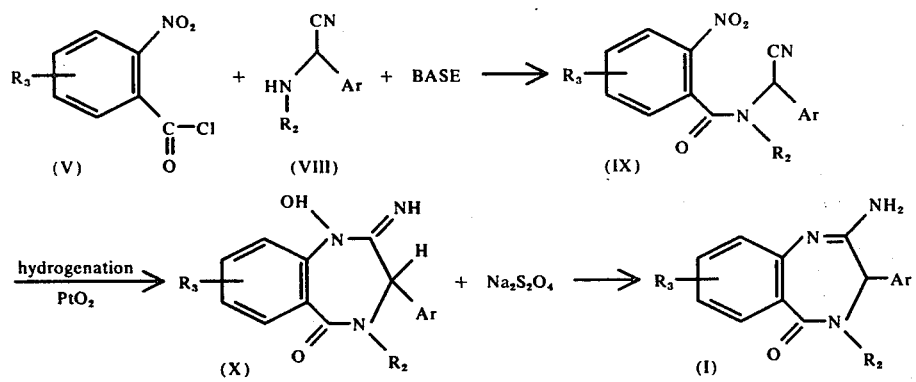

The compounds of formula (I) may be converted to the corresponding therapeutically active non-toxic acid addition salt form by reaction with an appropriate acid, such as, for example, an inorganic acid, such as, a hydrohalic acid, e.g., hydrochloric, hydrobromic, or hydroiodic acid, and sulfuric acid, nitric acid, phosphoric acid and the like; or an organic acid, such as, acetic, propionic, glycolic, lactic, pyruvic, malonic, succinic, maleic, fumaric, malic, tartaric, citric, benzoic, cinnamic, mandelic, methanesulfonic, ethanesulfonic, hydroxyethane-sulfonic, benzenesulfonic, p-toluenesulfonic, cyclohexanefulfamic, salicylic, p-aminosalicylic, 2-phenoxybenzoic, 2-aceloxybenzoic and the like acids. Conversely, the salt form can be converted by treatment with alkali into the free base form.

The compounds (I) of this invention are useful as CNS depressants and/or hypotensive agents. Specifically, the subject compounds wherein R is dihydroxyphenloweralkyl (dopamine analogs) or indolylloweralkyl (tryptamine analogs) have been observed to produce a decrease in blood pressure of about 40-120 mm Hg when administered i.v. to anesthetized dogs in a dose of about 10 mg/kg body weight. Compounds of formula (I) in which R is (i) arylloweralkyl other than the dihydroxyphenloweralkyl dopamine analogs mentioned above, or (ii) diloweralkyl-aminoloweralkyl, or (iii) the compounds wherein R is hydrogen and $R_1$ is, necessarily, aryl, possess useful central nervous system (CNS) depressant properties as demonstrated in one or more of the following tests indicative of such activity in laboratory animals. The remaining formula (I) compounds possess both the aforementioned hypotensive property and said CNS depressant properties as demonstrated in one or more of the following tests.

Test A

A muscle-relaxant assay as judged by the effect of the compound to be tested on strychnine-induced seizures as described by M. J. Orloff et al., Proc. Soc. Exp. Biol. and Med. 70, 254 (1949) as modified by G. Chen and B. Bohner, J. Pharmacol. and Expt. Therap. 117, 142 (1956). The anti-strychnine activity of the compound to be tested is observed in mice at oral doses of about 25-500 mg./kg. body weight by determining the effect of the compound on the seizure threshold induced by strychnine.

Test B

A muscle-relaxant assay as judged by the effect of the compound to be tested on metrazole-induced seizures as described by M. J. Orloff et al., Proc. Soc. Exp. Biol. and Med. 70, 254 (1949). The anti-metrazole activity of the compound to be tested is observed in mice at oral doses of about 25-500 mg./kg. body weight be determining the effect of the compound on the seizure thresholds induced by metrazole.

Test C

An anti-convulsant assay which is a supra-maximal electroshock seizure test as described by E. A. Swinyard et al., J. Pharmacol Expt. Therap. 106, 319 (1952). In this assay, the compound to be tested is administered orally to mice at doses generally ranging from 25-500 mg./kg. body weight and the blocking effect of the compound on the tonic extensor seizure following the application of a supramiximal current to the animal is observed.

Test D

A mouse behaviorial assay as described by S. Irwin, Gordon Research Conference on Medicinal Chemistry, 1959, p. 133. In this assay, such symptoms as ataxia, decrease in motor activity and loss or righting reflex are observed after intraperitoneal (i.p.) administration in mice of the compound to be tested at doses ranging from 10-300 mg./kg. body weight.

The following examples are intended to illustrate, but not to limit the scope of the present invention.

EXAMPLE I

A.

7-Chloro-3,4-dihydro-4-methyl-2-thio-1H-1,4-benzodiazepine-2,5-dione

A stirred mixture of 67.4 g (0.30m) of 7-chloro-3,4-dihydro-4-methyl-1H-1,4-benzodiazepine-2,5-dione and 26.7 g (0.12m) of phosphorous pentasulfide in 750 ml of pyridine is heated on a steam bath of 18½ The reaction mixture is concentrated to dryness in vacuo and partitioned between 300 ml of chloroform and 300 ml of cold 10% NaOH. The layers are separated and the organic (lower) layer is extracted with three 100 ml portions of 10% NaOH. The combined aqueous extracts are cooled in an ice bath and acidified with 110 ml of concentrated HCl causing the product to precipitate. The solid is filtered off, washed with water, and recrystallized from dimethylformamide-water to give a bright yellow solid. A second recrystallization from dimethylformamide-water (30:1) gives the pure product, 7-chloro-3,4-dihydro-4-methyl-2-thio-1H-1,4-benzodiazepine-2,5-dione, as a yellow solid, m.p. (264s) 271°- 275° C. (dec).

B. 2-Benzylamino-7-chloro-3,4-dihydro-4-methyl-5H-1,4-benzodiazepine-5-one

A stirred mixture of 6.74 g (0.028 m) of 7-chloro-3,4-dihydro-4-methyl-2-thio-1H-1,4-benzodiazepine-2,5-dione and 3.00 g (0.028 m) of benzyl amine in 100 ml of acetonitrile is heated to reflux while sweeping with nitrogen for 3 hr. The resulting solution is filtered to clarify and then concentrated to dryness in vacuo giving 9.2 g of an oily residue which is dissolved in 100 ml of benzene and extracted with five 20 ml portions of 10% NaOH and one 20 ml portion of saturated NaCl solution. The benzene solution is dried (anhydrous) $MgSO_4$ and concentrated to dryness in vacuo giving an oil which crystallizes when triturated with ether. The resulting solid is ground well under ether and the slurry is filtered to give 2-benzylamino-7-chloro-3,4-dihydro-4-methyl-5H-1,4-benzodiazepine-5-one, m.p. (153 s) 158° – 160° C. Two recrystallizations from ethyl acetate-ether give the pure product, m.p. 158° – 159.5° C.

EXAMPLE II

The procedure of Example I is repeated except that an equivalent amount of each of p-trifluoromethylbenzyl amine, 2,4,6-tribromobenzyl amine and 2,4-dimethylbenzyl amine is substituted for the benzyl amine used in part B to yield, as respective products, the following:

2-(p-trifluoromethylbenzylamino)-7-chloro-3,4-dihydro-4-methyl-5H-1,4-benzodiazepine-5-one;

2-(2,4,6-tribromobenzylamino)-7-chloro-3,4-dihydro-4-methyl-5H-1,4-benzodiazepine-5-one; and 2-(2,4-dimethylbenzylamino)-7-chloro-3,4-dihydro-4-methyl-5H-1,4-benzodiazepine-5-one.

EXAMPLE III 3,4-Dihydro-4-methyl-2-β-phenethylamino-5H-1,4-benzodiazepine-5-one A solution of 17.0 g (0.14 m) of β-phenethylamine in 100 ml dry tetrahydrofuran (THF) is added to a stirred suspension of 6.65 g (0.035 m) of 3,4-dihydro-4-methyl-5H-1,4-benzodiazepine-2,5-dione in 125 ml dry THF over a 3 minute period under a nitrogen atmosphere. A solution of 7.31 g (4.25 ml) (0.0385 m) of titanium tetrachloride in 225 ml dry THF [CAUTION: Violent exothermic reaction occurs when $TiCl_4$ is added to THF with copious evolution of fumes.] is added over a 30 minute period to the stirred reaction. Stirring is continued at room temperature for 30 minutes and at reflux overnight. The reaction is cooled to room temperature and an additional 4.24 g (0.035 m) of phenethylamine in 25 ml dry THF is added over a 5 minute period and the reaction stirred for an additional 5 hour at room temperature. Then 95 ml of $H_2O$ is added (dropwise at first and then in a steady stream), the slurry is filtered and the filtrate is evaporated to dryness in vacuo giving a mixture of solid and oil which is extracted with ether and then ethyl acetate leaving behind phenethylamine hydrochloride. The soluble portion is evaporated to dryness in vacuo and redissolved in $CHCl_3$. The chloroform solution is extracted with 10% HCl and then with 10% NaOH, dried and evaporated to dryness in vacuo giving an oil residue. The acid solution above is made basic with 50% and NaOH and extracted with $CHCl_3$. This chloroform solution is dried and evaporated to dryness in vacuo giving an oil. Both fractions of oil crystallize when treated with ether giving the crude product, 3,4-dihydro-4-methyl-2-β-phenethylamino-5H-1,4-benzodiazepine-5-one. Two recrystallizations from ethyl acetate gives the pure product as soft white needles, m.p. 150° – 151° C.

EXAMPLE IV

The procedure of Example III is repeated except that an equivalent amount each of p-butyl-β-phenethyl amine, 2,4,6-trimethyl-β-phenethyl amine, and 3-chloro-β-phenethyl amine is substituted for the β-phenethyl amine used therein to yield, as respective products, the following:

2-(p-butyl-β-phenethylamino)-3,4-dihydro-4-methyl-5H-1,4-benzodiazepine-5-one;

2-(2,4,6-trimethyl-β-phenethylamino)-3,4-dihydro-4-methyl-5H-1,4-benzodiazepine-5-one;

2-(3-chloro-β-phenethylamino)-3,4-dihydro-4-methyl-5H-1,4-benzodiazepine-5-one.

EXAMPLE V

7-Chloro-3,4-dihydro-4-methyl-2-phenethylamino-5H-1,4-benzodiazepine-5-one

A mixture of 13.24 g (0.055 m) of 7-chloro-3,4-dihydro-4-methyl-2-thio-5H-1,4-benzodiazepine-2,5-dione prepared according to the method described in Example I-A, and 6.06 g (0.05 m) of β-phenethylamine in 150 ml of acetonitrile is stirred and refluxed for 25 hours. The reaction mixture is cooled and filtered to give the crude product, 7-chloro-3,4-dihydro-4-methyl-2-phenethylamino-5H-1,4-benzodiazeine-5-one. Recrystallization from ethyl acetate and from ethanol/ether gives the pure product, m.p. 196.5° – 198° C.

EXAMPLE VI

By utilizing an equivalent amount of 4-hydroxy-3,5-dimethyl-β-phenethyl amine for the phenethyl amine in the procedure of Example V, 7-chloro-3,4-dihydro-2-(4-hydroxy-3,5-dimethyl phenethylamino)-4-methyl-5H-1,4-bezodiazepine-5-one is obtained as the product.

EXAMPLE VII

7-Chloro-3,4-dihydro-2-(3,4-dimethoxy-β-phenethylamino)-4-methyl-5H-1.4-benzodiazepine-5-one A solution of 25.4 g (0.14 m) of redistilled homoveratryl amine in 100 ml of dry tetrahydrofuran is added in a slow stream over a 5 minute period to a stirred suspension of 7.87 g (0.035 n) of 7-chloro-3,4-dihydro-4-methyl-5H-1,4-benzodiazepine-2,5-dione in 150 ml of dry tetrahydrofuran under a nitrogen atmosphere. Then a solution of 7.96 g (4.63 ml; 0.042 m) of titanium tetrachloride in 450 ml of dry tetrahydrofuran [CAUTION: A vigorous, exothermic reaction occurs when the titanium tetrachloride is added to the tetrahydrofuran and copious fumes are emitted.] is added dropwise to the stirred reaction mixture over a 60 minute period without cooling. Stirring is continued for 1 hour at room temperature and at reflux for 21 hours. The reaction mixture is allowed to cool to about 30° C and an additional 6.35 g (0.035 m) of homoveratrylamine in 25 ml of dry tetrahydrofuran is added over a 15 minute period. Stirring is continued for 5 hours more. Then 95 ml $H_2O$ is added, the slurry is filtered, and the filtrate concentrated to dryness in vacuo giving an oily residue. This residue is dissolved in chloroform, extracted with 10% hydrochloric acid and 10% sodium hydroxide, dried and concentrated to dryness in vacuo to give an oil (which crystallizes on standing). Recrystallization from ethyl acetate gives the solid product, 7-chloro-3,4-dihydro-2-(3,4-dimethoxy-β-phenethylamino)-4-methyl-5H-1,4-benzodiazepine-5-one, melting at 175° – 178° C. The acid extract above is made basic and extracted with chloroform. The chloroform solution is dried and concentrated to dryness in vacuo giving an oil which crystallizes when treated with ether. Filtration of this mixture leads to recovery of a solid product melting at 150°– 159° C. The two batches of solid product are combined and recrystallized twice from alcohol-ether giving the pure product, 7-chloro-3,4-dihydro-2-(3,4-dimethyl-β-phenethylamino)-4-methyl-5H-1,4-benzodiazepine-5-one, a white solid with m.p. 177.5° – 179.0° C.

EXAMPLE VIII

The procedure of Example VII is repeated except that an equivalent amount each of 3-methoxyphenethyl amine, 3,4-dimethoxy-2-methylphenethyl amine, and 4-methoxyphenethyl amine is substituted for the homoveratryl amine used therein to yield, as respective products, the following:

7-chloro-3,4-dihydro-2-(3-methoxyphenethylamino)-4-methyl-5H-1,4-benzodiazepine-5-one;

7-chloro-3,4-dihydro-2(3,4-dimethoxy-2-methylphenethylamino)-4-methyl-5H-1,4-benzodiazepine-5-one; and 7-chloro-3,4-dihydro-2(4-methoxyphenethylamino)-4-methyl-5H-1,4-benzodiazepine-5-one.

EXAMPLE IX 3,4-Dihydro-2-(3,4-dihydroxyphenethylamino)-4-methyl-5H-1,4-benzodiazepine-5-one Hydrochloride Hemimethanolate A mixture of 8.42 g (0.035 m) of 7-chloro-3,4-dihydro-4-methyl-2-thio-1H-1,4-benzodiazepine-2,5-dione and 11.67 g (0.035 m) of 3,4-dibenzyloxy-β-phenethylamine in 150 ml of acetonitrile is stirred and refluxed for 17 hours. The reaction mixture is concentrated to dryness in vacuo to give an oily residue. This residue is dissolved in benzene and washed with 1N sodium hydroxide solution and 3N hydrochloric acid to give a gummy residue. This gum is dissolved in methanol, diluted with an equal volume of benzene, treated with charcoal, filtered and concentrated to dryness in vacuo to give crude 7-chloro-2-(3,4-dibenzyloxyphenethylamino)-3,4-dihydro-4-methyl-5H-1,4-benzodiazepine-5-one. The free base is converted in ethanol/ether to the hydrochloride salt to give a white solid, with m.p. (153 softens) 158°– 162° C.

A mixture of 11.34 g (0.0197 m) of 7-chloro-2-(3,4-dibenzyloxyphenethylamino)-3,4-dihydro-4-methyl-5H-1,4-benzodiazepine-5-one hydrochloride and 10% palladium on charcoal catalyst in 250 ml of absolute methanol is hydrogenated until no more hydrogen is absorbed. The catalyst is removed by filtration and the filtrate is concentrated to dryness in vacuo to give crude 3,4-dihydro-2-(3,4-dihydroxyphenethylamino)-4-methyl-5H-1,4-benzodiazepine-5-one hydrochloride hemi methanolate. Several recrystallizations from ethanol/ether give the pure product, m.p. 179° – 180° C. dec.

EXAMPLE X

The procedure of Example IX is repeated except that an equivalent amount of 2,4,5-tribenzyloxyphenethyl amine is substituted for the 3,4-dibenzyloxyphenethyl amine used therein to yield the product:

3,4-dihydro-4-methyl-2-(2,4,5-trihydroxyphenethylamino)-5H-1,4-benzodiazepine-5-one.

EXAMPLE XI

A.

7-Chloro-3,4-dihydro-4-methyl-2-methylthio-5H-1,4-benzodiazepine-5-one

A solution of 0.69 g (0.0055 m) of dimethyl sulfate in 2.5 ml of methanol is added dropwise at room temperature to a stirred mixture of 1.20 g (0.005 m) of 7-chloro-3,4-dihydro-4-methyl-2-thio-1H-1,4-benzodiazepine-2,5-dione prepared according to the method described in Example I-A in 6.0 ml 1N sodium hydroxide solution and 7.5 ml of methanol. The reaction mixture is stirred at room temperature for 45 minutes after which time 10 ml of water is added and the pH adjusted to 11 by the addition of 3.0 ml 5N sodium hydroxide solution. The mixture is cooled and the precipitate removed by filtration. The solid is washed with water and dried to give yellow compound, 7-chloro-3,4-dihydro-4-methyl-2-methylthio-5H-1,4-benzodiazepine-5-one, m.p. 124° – 127° C.

B.

7-Chloro-2-(2',6'-dichloroanilino)-3,4-dihydro-4-methyl-5H-1,4-benzodiazepine-5-one A mixture of 20.38 g (0.08 m) of 7-chloro-3,4-dihydro-4-methyl-2-methylthio-5H-1,4-benzodiazepine-5-one and 64.81 g (0.40 m) of 2,6-dichloroaniline is stirred and heated to 225° for 1 ½ hr. The reaction mixture is cooled to room temperature and crystallized from ether to give the crude product, 7-chloro-2-(2',6'-dichloroanilino)-3,4-dihydro-4-methyl-5H-1,4-benzodiazepine-5-one, m.p. (230) 240° – 245°. Recrystallization from acetone-ether and from methanol-isopropanol gives white solid with m.p. 247° – 249.5°.

EXAMPLE XII

7-Chloro-3,4-dihydro-2-[3-(dimethylamino)-propylamino]-4-methyl-5h-1,4-benzodiazepine-5-one Dihydrochloride A stirred mixture of 10.7 g (0.045 m) of 7-chloro-3,4-dihydro-4-methyl-2-thio-1H-1,4-benzodiazepine-2,5-dione prepared as described in Example I-A, and 5.51 g (0.054 m) of dimethylaminopropylamine in 100 ml of acetonitrile is heated on a steam bath at reflux, while sweeping with nitrogen, for 4 ½ hours. The resulting solution is concentrated to dryness in vacuo giving an oily residue which is then dissolved in anhydrous ether. A saturated solution of ethereal HCl is added to precipitate the dihydrochloride salt. The solution is filtered and the solid is recrystallized once from methanol-ether and again from methanol giving the light yellow solid product, 7-chloro-3,4-dihydro-2-[3-(dimethylamino)-propylamino]-4-methyl-5H-1,4-benzodiazepine-5-one, m.p. 261° – 264° C (dec.).

EXAMPLE XIII

Utilizing an equivalent amount of diethylaminoethylamine in place of dimethylaminopropylamine in the procedure of Example XII results in the product:

7-Chloro-3,4-dihydro-2-[2-(diethylamino)ethylamino]-4-methyl-5H-1,4-benzodiazepine-5one dihydrochloride.

EXAMPLE XIV

7-Chloro-3,4-dihydro-2-[2-(3-indolylethyl) amino]-4-methyl-5H-1,4-benzodiazepine-5one A mixture of 8.43 g (0.035 m) of 7-chloro-3,4-dihydro-4-methyl-2-thio-1H-1,4-benzodiazepine-2,5-dione and 5.61 g (0.035 m) of tryptamine in 150 ml of acetonitrile is stirred and refluxed for 4 ½ hours. The reaction mixture is concentrated to about 80 ml, cooled and filtered to give the solid product. Recrystallization from methyl ethylketone/ether (125 ml: 375 ml) gives the pure product, 7-chloro-3,4-dihydro-2-[2-(3-indolylethyl) amino]-4-methyl-5H-1,4-benzodiazepine-5-one, m.p. 220° – 222° C.

EXAMPLE XV

The procedure of Example XIV is repeated except that an equivalent amount of each of 3,4-dihydro-4-methyl-7-nitro-2-thio-1H-1,4-benzodiazepine-2,5-dione, 3,4-dihydro-4-methyl-7-methyl-2-thio-1H-1,4-benzodiazepine-2,5-dione, 3,4-dihydro-8-ethoxy-4-methyl-1H-1,4-benzodiazepine-2,5-dione is substituted for the 7-chloro-3,4-dihydro-4-methyl-2-thio-1H-1,4-benzodiazepine-2,5-dione used therein, to yield, as respective products the following:

3,4-dihydro-2-[2-(3-indolylethyl) amino]-4-methyl-7-nitro-5H-1,4-benzodiazepine-5-one;

3,4-dihydro-2-[2-(3-indolylethyl) amino]-4-methyl-7-methyl-5H-1,4-benzodiazepine-5-one;

3,4-dihydro-8-ethoxy-2-[2-(3-indolylethyl) amino-4-methyl-5H-1,4-benzodiazepine-5-one.

EXAMPLE XVI

A. β-Methyl-o-nitro-α-phenylhippuronitrile

A solution of 92.78 g (0.5 m) of o-nitro benzoyl chloride in 100 ml of dry 1,2-dichloroethane is added dropwise over a 90 minute period to a stirred, ice cooled solution of 73.10g (0.5m) of N-methyl-α-phenyl glycinitrile and 55.66 g (0.55 m) of triethylamine in 400 ml of dry 1,2-dichloro-ethane. After stirring the reaction mixture for 4 ½ hours at room temperature, 200 ml of water is added. The layers are separated and the organic layer is washed with two 150 ml portions of 1N hydrochloric acid five 100 ml portions of 1N sodium hydroxide and two 100 ml portions of saturated sodium chloride solution. The organic layer is dried and concentrated to dryness in vacuo to give an oily residue of β-methyl-o-nitro-α-phenyl hippuronitrile which may be used without further purification in the next step.

B.

1-Hydroxy-2-imino-4-methyl-3-phenyl-1,2,3,4-tetrahydro-5H-1,4-benzodiazepine-5-one hydrochloride A solution of 14.77 g (0.05 m) of β-methyl-o-nitro-α-phenyl hippuronitrile in 500 ml of absolute ethanol containing 0.20 g of platinum oxide is hydrogenated at room temperature on a Parr shaker at an initial pressure of 50 psi. Hydrogen absorption is complete in about 1 hour. The catalyst is removed by filtration, and the filtrate concentrated to dryness in vacuo to give an impure solid. Trituration with ether, followed by recrystallization from isopropanol gives the solid, 1-hydroxy-2-imino-4-methyl-3-phenyl-1,2,3,4-tetrahydro-5H-1,4-benzodiazepine-5-one. This is converted to the hydrochloride salt in ethanol and recrystallized from ethanol/ether (50 ml:200 ml) giving pure 1-hydroxy-2-inino-4-methyl-3-phenyl-1,2,3,4-tetrahydro-5H-1,4-benzodiazepine-5-one hydrochloride, a solid, m.p. 223° C (dec). Conventional treatment with alkali (e.g. NaOH) affords the corresponding free base form.

C.

2-Amino-3,4-dihydro-4-methyl-3-phenyl-5H-1,4-benzodiazepine-5-one

A slow stream of a solution of 23.00 g (0.132 m) of sodium dithionite in 300 ml of water is added to a stirred solution of 16.87 g (0.06 m) of 1-hydroxy-2-imino-4-methyl-3-phenyl-1,2,3,4-tetrahydro-5H-1,4-benzodiazepine-5-one in 700 ml of ethanol. The reaction mixture is refluxed for 2 hours and then concentrated in vacuo, to about 200 ml. The resulting solution is extracted once with chloroform. Some solid crude product, formed during this extraction, is filtered off. The aqueous layer is made basic and extracted with chloroform. The organic solutions are combined, dried and concentrated to dryness in vacuo to give additional solid product. The solids are combined and recrystallized twice from ethanol/ether (the solution is filtered while hot to clarify) to give the pure product, 2-amino-3,4-dihydro-4-methyl-3-phenyl-5H-1,4-benzodiazepine-5-one m.p. 282° – 286° C.

EXAMPLE XVII

A. The procedure of Example XVI-A is repeated except that an equivalent amount each of the following compounds are used in place of N-methyl-α-phenylglycinitrile used therein: N-methyl-α-(2,4,6-trichlopheny) glycinitrile, N-methyl-α-(3,4-dimethoxyphenyl) glycinitrile, N-methyl-α-(2-bromo-4-methylpheny) glycinitrile, and N-ethyl-α-(4-trifluoromethylphenyl) glycinitrile to yield the following as respective products:

β-methyl-o-nitro-α-(2,4,6-trichlorophenyl) hippuronitrile;

β-methyl-o-nitro-α-(3,4-dimethoxyphenyl) hippuronitrile;

β-methyl-o-nitro-α-(2-bromo-4-methylphenyl) hippuronitrile;

β-ethyl-o-nitro-α-(4-trifluoromethylphenyl) hippuronitrile.

B. An equivalent amount of each of the foregoing precursors is substituted for the α-phenyl derivative used in Example XVI-B to produce the corresponding 3-substituted-phenyl intermediates.

C. These 3-substituted phenyl intermediates, each used in an equivalent amount as the 1-hydroxy-2-imino-4-methyl-3-phenyl-1,2,3,4-tetrahydro-5H-1,4-benzodiazepine-5-one of Example XVI-C, produce the corresponding 3-substituted phenyl end products.

EXAMPLE XVIII

A. β-Methyl-o-nitro-α-phenyl hippuric acid

A solution of 92.78 g (0.5 m) of o-nitrobenzoyl chloride in 150 ml of chloroform is added dropwise to a vigorously stirred solution of 100.87 g (0.5 m) of α-phenyl sarcosine HCl and 40.00 g (1.0 m) of sodium hydroxide in 750 ml of water while cooling in an ice bath. The reaction mixture is stirred for 5 hours at room temperature while periodically adding 5N sodium hydroxide solution (150 ml used) to keep the reaction basic. The precipitated solid is then removed by filtration and the resulting layers are separated. The aqueous layer is cooled, acidified with concentrated hydrochloric acid, and extracted with ethyl acetate. The ethyl acetate solution is dried and concentrated to dryness in vacuo. The resulting solid is triturated with ether/hexane (200 ml/100 ml) and filtered to give the solid product β-methyl-o-nitro-α-phenyl hippuric acid, m.p. 170° - 179° C.

B.
3,4-Dihydro-4-methyl-3-phenyl-1H-1,4-benzodiazepine-2,5-dione

A mixture of 47.2 g (0.15 m) of β-methyl-o-nitro-α-phenyl hippuric acid and 1.0 g of platinum oxide in 750 ml of 95% ethanol is hydrogenated in a Parr Hydrogenator, with cold water in the cooling jacket, at a constant pressure of 20 psi for 1 hour and at a constant pressure of 30 psi for ½ hour. The catalyst is filtered away and the filtrate is concentrated almost to dryness in vacuo to give an oily residue. The oil is then dissolved in 150 ml of dimethylformamide and boiled down to 75 ml. The addition of 25 ml of water and cooling causes the product, 3,4-dihydro-4-methyl-3-phenyl-1H-1,4-benzodiazepine-2,5-dione to crystallize, having a m.p. of 242° - 243° C. Recrystallization from dimethylformamide/water gives a pure product, 3,4-dihydro-4-methyl-3-phenyl-1H-1,4-benzodiazepine-2,5-dione m.p. 242° - 244° C.

C.
3,4-Dihydro-4-methyl-3-phenyl-2-thio-1H-1,4-benzodiazepine-2,5-dione

A mixture of 26.63 g (0.10 m) of 3,4-dihydro-4-methyl-3-phenyl-1H-1,4-benzodiazepine-2,5-dione and 4.67 g (0.021 m) of phosphorous pentasulfide in 250 ml of pyridine are stirred and heated to reflux for 1 ½ hr. 150 ml of pyridine is distilled off and then the reaction mixture is refluxed for 1 ½ hr. more. The hot reaction mixture is added to 150 ml hot water and the mixture is stirred for ½ hr. The precipitate is removed by filtration, washed with water and dried to give the solid product 3,4-dihydro-4-methyl-3-phenyl-2-thio-1H-1,4-benzodiazepine-2,5-dione, m.p. 250.5° - 225° C.

D.
3,4-Dihydro-4-methyl-2-methylthio-3-phenyl-5H-1,4-benzodiazepine-5-one

A solution of 10.10 g (0.08 m) of dimethyl sulfate in 40 ml of methanol is added dropwise at room temperature to a stirred mixture of 22.59 g of 3,4-dihydro-4-methyl-3-phenyl-2-thio-1H-1,4-benzodiazepine-2,5-dione, 80 ml of 1N sodium hydroxide solution and 40 ml of methanol. The reaction mixture is stirred at room temperature for 5 hours, cooled in ice and the pH adjusted to about 11 with 10N sodium hydroxide solution. The precipitate is removed by filtration, washed with water and dried to give 22.42 g of solid 3,4-dihydro-4-methyl-2-methylthio-3-phenyl-5H-1,4-benzodiazepine-5-one, m.p. 130° - 132° C.

E.
3,4-Dihydro-4-methyl-2-phenethylamino-3-phenyl-5H-1,4-benzodiazepine-5-one

A mixture of 7.41 g (0.025 m) of 3,4-dihydro-4-methyl-2-methylthio-3-phenyl-5H-1,4-benzodiazepine-5-one and 12.11 g (0.100 m) of phenethylamine is heated in an oil bath for 6 hours. The temperature of the oil bath is slowly raised to 240° C and held there for 1 hour. After cooling to room temperature, the residual oil is crystallized from ether to give the crude product, 3,4-dihydro-4-methyl-2-phenethylamino-3-phenyl-5H-1,4-benzodiazepine-5-one. Recrystallization from ethyl and ethyl acetate-ether gives a pure product, 3,4-dihydro-4-methyl-2-phenethylamino-3-phenyl-5H-1,4-benzodiazepine-5-one, a while solid, m.p. 173° - 174.5° C.

EXAMPLE XIX 3,4-Dihydro-2-[2-(dimethylamino)ethylamino]-4-methyl-3-phenyl-5H-1,4-benzodiazepine-5-one Dihydrochloride Hemihydrate A mixture of 8.48 g (0.03 m) of 3,4-dihydro-4-methyl-3-phenyl-2-thio-1H-1,4-benzodiazepine-2,5-dione and 13.20 g (0.15 m) of β-dimethylaminoethylamine are heated in an oil bath at 145°±5° C under reflux for 25 minutes. The excess amine is removed in vacuo at 100° C and the residue is triturated with ether to give solid 3,4-dihydro-2-[2-(dimethyl-amino) ethylamino]-4-methyl-3-phenyl-5H-1,4-benzodiazepine-5-one dihydrochloride hemihydrate, m.p. (240°) 246° - 250° C (dec).

What is claimed is:
1. A compound having the formula:

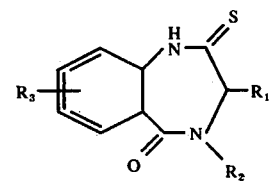

wherein:
$R_1$ is a member selected from the group consisting of hydrogen and aryl, said aryl being a member selected from the group consisting of phenyl, trifluoromethylphenyl and phenyl substituted with from 1 to 3 members selected from the group consisting of halo, loweralkyl, hydroxy, and loweralkoxy;
$R_2$ is loweralkyl; and
$R_3$ is a member selected from the group consisting of hydrogen, halo, nitro, loweralkoxy and loweralkyl.

2. A compound having the formula:

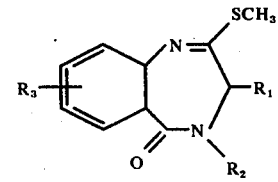

wherein:
$R_1$ is a member selected from the group consisting of hydrogen and aryl, said aryl being a member selected from the group consisting of phenyl, trifluoromethylphenyl and phenyl substituted with from 1 to 3 members selected from the group consisting of halo, loweralkyl, hydroxy and loweralkoxy;
$R_2$ is loweralkyl; and
$R_3$ is a member selected from the group consisting of hydrogen, halo, nitro, loweralkoxy and loweralkyl.

* * * * *

UNITED STATES PATENT AND TRADEMARK OFFICE
CERTIFICATE OF CORRECTION

PATENT NO. : 4,031,079
DATED : June 21, 1977
INVENTOR(S) : Richard J. Mohrbacher & Philip P. Grous It is certified that error appears in the above-identified patent and that said Letters Patent are hereby corrected as shown below:

In Column 3, line 50, "-oni-" should read "-o-ni-"
In Column 6, line 21, "be" should read ---by---
In Column 10, line 43, "-methyl-5h-" should read "-methyl-5H-"
In Column 11, line 4, "5one" should read "5-one"
In Column 11, line 11, "ethylketone" should read "ethyl ketone"

Signed and Sealed this

Ninth Day of May 1978

[SEAL]

Attest:

RUTH C. MASON
Attesting Officer

LUTRELLE F. PARKER
Acting Commissioner of Patents and Trademarks